United States Patent [19]

Atwater

[11] Patent Number: 5,238,905

[45] Date of Patent: * Aug. 24, 1993

[54] PLANT CONTROL COMPOSITION AND METHODS OF USE WITH THIDIAZURON AND MONOCARBAMIDE DIHYDROGEN SULFATE

[75] Inventor: Mark L. Atwater, Iron City, Ga.

[73] Assignee: Union Oil Company of California, Los Angeles, Calif.

[ * ] Notice: The portion of the term of this patent subsequent to Jun. 22, 2010 has been disclaimed.

[21] Appl. No.: 828,613

[22] Filed: Jan. 31, 1992

Related U.S. Application Data

[63] Continuation-in-part of Ser. No. 783,535, Oct. 28, 1991.

[51] Int. Cl.$^5$ ...................... A01N 43/82; A01N 47/34
[52] U.S. Cl. .................................. 504/139; 504/148; 504/170
[58] Field of Search .......................... 71/69, 73, 110; 504/139, 148, 170

[56] References Cited

U.S. PATENT DOCUMENTS

| | | | |
|---|---|---|---|
| 3,799,758 | 3/1974 | Franz | 71/86 |
| 3,883,547 | 5/1975 | Schulz et al. | 260/306.8 |
| 4,199,345 | 4/1980 | Franz | 71/86 |
| 4,214,888 | 7/1980 | Young | 71/28 |
| 4,233,056 | 11/1990 | Maier | 71/86 |
| 4,294,605 | 10/1981 | Arndt et al. | 71/73 |
| 4,310,343 | 1/1982 | Verdegaal et al. | 71/28 |
| 4,315,763 | 2/1982 | Stoller et al. | 71/29 |
| 4,366,232 | 12/1982 | Buser et al. | 430/390 |
| 4,397,675 | 8/1983 | Young | 71/28 |
| 4,402,852 | 9/1983 | Young | 252/182 |
| 4,404,116 | 9/1983 | Young | 252/182 |
| 4,405,531 | 9/1983 | Franz | 260/501.12 |
| 4,445,925 | 5/1984 | Young | 71/28 |
| 4,447,253 | 5/1984 | Young | 71/28 |
| 4,512,813 | 4/1985 | Young | 134/27 |
| 4,522,644 | 6/1985 | Young | 71/78 |
| 4,589,925 | 5/1986 | Young | 134/3 |
| 4,626,417 | 12/1986 | Young | 423/235 |
| 4,664,717 | 5/1987 | Young | 127/37 |
| 4,673,522 | 6/1987 | Young | 252/87 |
| 4,686,017 | 8/1987 | Young | 204/45.1 |
| 4,722,986 | 2/1988 | Young | 527/203 |
| 4,743,669 | 5/1988 | Young | 527/200 |
| 4,755,265 | 7/1988 | Young | 204/45.1 |
| 4,801,511 | 1/1989 | Young | 429/198 |
| 4,818,269 | 4/1989 | Young | 71/83 |
| 4,831,056 | 5/1989 | Young | 514/588 |
| 4,834,788 | 5/1989 | Young | 71/83 |
| 4,839,088 | 6/1989 | Young | 252/182.27 |
| 4,877,869 | 10/1989 | Young | 536/35 |
| 4,879,413 | 11/1989 | Buser et al. | 564/63 |
| 4,885,425 | 12/1989 | Young | 585/458 |
| 4,910,179 | 3/1990 | Young | 437/228 |
| 4,910,356 | 3/1990 | Young | 585/262 |
| 4,912,278 | 3/1990 | Young | 585/458 |
| 4,931,061 | 6/1990 | Young | 47/57.6 |

(List continued on next page.)

FOREIGN PATENT DOCUMENTS

| | | |
|---|---|---|
| 0243522 | 11/1987 | European Pat. Off. . |
| 0271173 | 6/1988 | European Pat. Off. . |
| 2367427 | 5/1978 | France . |
| 2121686 | 1/1984 | United Kingdom . |

OTHER PUBLICATIONS

Donald C. Young, U.S. Ser. No. 07/313,188, filed Feb. 21, 1989, for Cellulosic Compositions.
Donald C. Young, U.S. Ser. No. 07/150,224, filed Jan. 29, 1988, for Isomerization.
Donald C. Young, U.S. Ser. No. 07/546,571, filed Jun. 28, 1990, for Adduct Compositions.
Donald C. Young, U.S. Ser. No. 07/707,322, filed Dec.

(List continued on next page.)

*Primary Examiner*—Richard L. Raymond
*Assistant Examiner*—B. Bembenick
*Attorney, Agent, or Firm*—Gregory F. Wirzbicki; Shlomo R. Frieman

[57] ABSTRACT

Compositions and methods for vegetation control comprise synergistic combinations of a thiazol-urea abscission agent and an adduct formed by the reaction of sulfuric acid with an amide. The synergistic combinations are particularly useful for the defoliation of cotton.

30 Claims, No Drawings

U.S. PATENT DOCUMENTS

| | | | |
|---|---|---|---|
| 4,931,079 | 6/1990 | Young | 71/77 |
| 4,935,048 | 6/1990 | Young | 71/83 |
| 4,942,254 | 7/1990 | Young | 558/250 |
| 4,944,787 | 7/1990 | Young | 71/28 |
| 4,966,620 | 10/1990 | Young | 71/83 |
| 4,993,442 | 2/1991 | Young | 134/22.14 |
| 4,994,101 | 2/1991 | Young | 71/83 |
| 5,034,046 | 7/1991 | Young | 55/213 |
| 5,035,737 | 7/1991 | Young | 71/83 |
| 5,055,127 | 10/1991 | Young | 71/83 |
| 5,057,584 | 10/1991 | Young | 526/220 |
| 5,099,014 | 3/1992 | Young | 540/145 |
| 5,105,040 | 4/1992 | Young | 585/425 |
| 5,105,043 | 4/1992 | Young | 585/477 |
| 5,116,401 | 5/1992 | Young | 71/86 |
| 5,116,916 | 5/1992 | Young | 525/350 |

OTHER PUBLICATIONS 27, 1990, for Systemic Herbicides and Methods of Use.

Donald C. Young, U.S. Ser. No. 07/343,489, filed Apr. 25, 1989, for Pesticidal Compositions and Methods for Controlling Pests.

D. F. duToit, Verslag Akad. Wetenschappen, 22 5/3-4 (Abstracted in Chemical Abstracts, 8, 2346 (1914).

L. H. Dalman, "Ternary Systems of Urea and Acids. I. Urea, Nitric Acid and Water. II. Ura, Sulfuric Acid and Water. III. Urea, Oxalic Acid and Water"; JACS 56, 549-53 (1934).

Sulfur Institute Bulletin No. 10 (1964), "Adding Plant Nutrient Sulfur to Fertilizer".

E. Grossbard and D. Atkinson, "The Herbicide Glyphosate," Butterworths, Boston, 1985 (pp. 221-240).

Comparative Phytotoxicity of Glyphosate, SC-0224, SC-0545, and HOE-00661, Carlson and Burnside, Weed Science, 1984, 32, 841-844.

"Complexing Agents as Herbicide Additives," Turner and Loader, Weed Research, 1978, 18, 199-207.

"Effect of Water Quality, Carrier Volume and Acid on Glyphosate Phytotoxicity," Buehler and Burnside, Weed Science, 1983, 31:163-169.

"New Weed Management Practices In Orchards," Neil H. Phillips, Proceedings, 36th Annual California Weed Conference, Jan. 16-19, 1984, Sacramento, Calif.

PLANT CONTROL COMPOSITION AND METHODS OF USE WITH THIDIAZURON AND MONOCARBAMIDE DIHYDROGEN SULFATE

This application is a continuation-in-part of application Ser. No. 07/783,535 filed Oct. 28, 1991, the disclosure of which is incorporated in its entirety by reference.

BACKGROUND OF THE INVENTION

1. Field of the Invention

The present invention relates to agents for controlling plant growth and methods for their use and preparation. The invention particularly relates to a combination of an abscission agent and an amide-sulfuric acid adduct, which combination is characterized by synergistic defoliation activity.

2. Description of the Art

Special tissue regions at the base of a leaf, flower or fruit stalk, are responsible for the separation of plant organs such as leaves, flowers and fruit from the plant body. When the separation process begins, the cell walls in the separation zone become soft so that the separation of the organ (abscission) becomes possible through mechanical forces, for example, by wind, or by weight of the organ itself. This, however, often does not take place at the desired time or to a desired extent. Frequently, it is advantageous to achieve this process in a controlled manner at a certain time or stage in the development of a plant.

Controlled defoliation is of special economic importance because of the easier harvesting and accelerated ripening obtainable thereby in agricultural and horticultural crops. Abscission agents for inducing such defoliation, via hormonal regulation, are known.

For example, thidiazuron, the common name for n-phenyl-n'-1,2,3-thiadiazol-5-yl urea, is a known cotton defoliant and has been registered for such purpose with the Environmental Protection Agency.

Defoliation also may be accomplished by leaf injury with certain herbicides. The herbicide may be of either the contact or systemic variety. A contact herbicide requires that a substantial portion of the plant be contacted with the active ingredient of the herbicide being applied. A systemic herbicide translocates through the plant and substantial surface contact is not required.

Many chemical agents have been found which are useful for the defoliation of plants, either through hormonal regulation or herbicidal injury, and have been registered with the Environmental Protection Agency for certain selected uses. Their effectiveness frequently varies greatly depending upon the climatic conditions, application rates, and the plant to which they are being applied. Thus, there still is need for an improved agent for effectively defoliating plants to facilitate harvest, for the destruction of plants for weed control, and the like.

SUMMARY OF THE INVENTION

The present invention resides in the discovery that a combination of an abscission agent and an amide-sulfuric acid adduct exhibit substantially enhanced plant control activity. The combination has been found to be more effective than when they are applied individually. This result often is termed potentiation or synergism since the combination demonstrates a potentency or activity level exceeding that which would be expected based on knowledge of the individual potencies of the components.

The abscission agent, as defined herein, is a plant tolerable agent which affects the cells at the base of the leaf stalk contacted. The adduct component of the present invention is generally used as a contact herbicide to destroy plants. A particularly surprising aspect of the present invention is that the claimed combination of agents appears to act in a synergistic manner to effect plant control, for example, by defoliation. In one very important discovery, it was found that the abscission agent and adduct could be used in combination in individual low concentrations (or in individual low application rates) that would render each essentially ineffective for its intended purpose—yet produce, through the combination, a highly efficacious abscission agent for defoliation. More specifically, when the abscission agent is applied at a rate ineffective by itself for significant defoliation in combination with the adduct applied at a rate ineffective by itself for significant herbicidal activity, the result is an abscission agent of high potency for defoliation. Accordingly, although the invention is not to be held to any theory of operation, it seems clear that in the combination of the invention the adduct, for unknown reasons, substantially increases the potency of the abscission agent, allowing for less of it to be used while still attaining the desired defoliation result.

A particularly preferred composition of the present invention is a combination of thidiazuron and monocarbamide dihydrogen sulfate. The preferred combination has been found to be particularly effective for the defoliation of cotton. In addition, post treatment regrowth of leaves on a treated plant is substantially inhibited by the combination of the present invention.

DETAILED DESCRIPTION OF THE INVENTION

It now has been found that synergism in the defoliation of plants is exhibited by a combination of a thiozol-urea abscission agent and an adduct produced by reaction of sulfuric acid and an amide. The thiozol-urea abscission agents of the present invention are characterized by the general formula

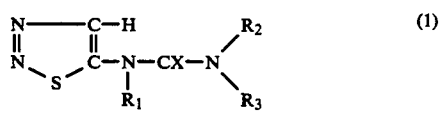

in which $R_1$ and $R_2$ are independently selected from the group consisting of $H_2$ and $C_1$ to $C_5$ organic radicals, $R_3$ is a $C_1$ to $C_{50}$ organic radical, preferably $C_1$ to $C_{20}$, more preferably $C_1$ to $C_{10}$, and X is an oxygen or sulfur atom.

Preferred compounds of the above general formula are those compounds in which the radical $R_1$ is hydrogen or alkyl with 1 to 3 carbon atoms, such as methyl or ethyl, the radical $R_2$ is hydrogen or alkyl with 1 to 4 carbon atoms, such as methyl or ethyl, the radical $R_3$ is alkyl with 1 to 4 carbon atoms, such as methyl or ethyl, cycyoalkyl with 5 to 8 carbon atoms, such as cyclopentyl, cyclohexyl or methylcyclohexyl, or a phenyl, halphenyl, methylphenyl or methoxyphenyl radical, and X is oxygen or sulfur. Particularly preferred compounds are those in which the radicals $R_2$ and $R_3$ jointly form with the N atom a morpholino, piperidino or pyrrolidino group.

Examples of methods for formulating such compounds are fond in U.S. Pat. Nos. 4,294,605, issued Oct. 13, 1981, and 3,883,547, issued May 13, 1975, which are incorporated herein in their entirety by reference. Exemplary compounds are set forth in Table A below in which the (D) following temperature refers to a decomposition temperature.

TABLE A

| Active Substance | Physical Constant |
|---|---|
| 1. N-phenyl-N'-(1,2,3-thiadiazole-5-yl) urea | M.P. 217° C. (D) |
| 2. N-ethyl-N-phenyl-N'-(1,2,3-thiadialol-5-yl) urea | M.P. 200° C. (D) |
| 3. N-(4-chlorophenyl)-N'-(1,2,3-thiadiazole-5-yl) urea | M.P. 256° C. (D) |
| 4. N-cyclohexyl-N-'-(1,2,3-thiadiazole-5-yl) urea | M.P. 215° C. (D) |
| 5. N-(chlorophenyl)-N'-(1,2,3-thiadiazole-5-yl) urea | M.P. 244° C. (D) |
| 6. N-(4-methylphenyl)-N'-(1,2,3-thiadiazole-5-yl) urea | M.P. 228° C. (D) |
| 7. N-(3-methylphenyl)-N'-(1,2,3-thiadiazole-5-yl) urea | M.P. 208° C. (D) |
| 8. N-(3,4-dichlorophenyl)-N'-(1,2,3-thiadiazole-5-yl) urea | M.P. 236° C. (D) |
| 9. N-methyl-N'-(1,2,3-thiadiazole-5-yl) urea | M.P. 174° C. |
| 10. N,N-dimethyl-N'-(1,2,3-thiadiazole-5yl) urea | M.P. 222° C. (D) |
| 11. N,N-dimethyl-N'-methyl-N'-(1,2,3-thiadiazole-5-yl) urea | M.P. 129° C. |
| 12. N-methyl-N'-methyl-N'-(1,2,3-thiadiazole-5-yl) urea | M.P. 221° C. |
| 13. N-methyl-N-phenyl-N'-(1,2,3-thiadiazole-5-yl) urea | M.P. 184° C. (D) |
| 14. N-ethyl-N-phenyl-N'-(1,2,3-thiadiazole-5-yl) urea | M.P. 200° C. (D) |
| 15. N-propyl-N-phenyl-N'-(1,2,3-thiadiazole-5-yl) urea | M.P. 190° C. (D) |
| 16. N-butyl-N-phenyl-N'-(1,2,3-thiadiazole-5-yl) urea | M.P. 198° C. (D) |
| 17. N-(2-chlorophenyl)-N'-(1,2,3-thiadiazole-5-yl) urea | M.P. 237° C. (D) |
| 18. N-(2-methylphenyl)-N'-(1,2,3-thiadiazole-5-yl) urea | M.P. 197° C. (D) |
| 19. N-(2-nitrophenyl)-N'-(1,2,3-thiadiazole-5-yl) urea | M.P. 229° C. (D) |
| 20. N-(3-nitrophenyl)-N'-(1,2,3-thiadiazolyl-5-yl) urea | M.P. 252° C. (D) |
| 21. N-methyl-N-(2-methylphenyl)-N'-(1,2,3-thiadiazole-5-yl) urea | M.P. 215° C. (D) |

The adducts for use in accordance with the present invention are produced by reacting sulfuric acid with an amide having the following formula:

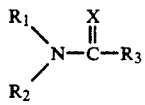

(2)

wherein X is a chalcogen, each of $R_1$, $R_2$ and $R_3$ is independently selected from hydrogen and monovalent organic radicals, and $R_1$ and $R_2$, together, can form a divalent organic radical. The molar ratio of amide to sulfuric acid is within the range of about ¼ to less than 2 so that at least some of the sulfuric acid is present as the monoamide-sulfuric acid adduct. As used herein, "amide" includes all compounds of formula (2) regardless of the chalcogen employed.

When $R_1$, $R_2$ and $R_3$ are organic radicals, they may be cyclic or acyclic, straight or branched chained and can contain one or more hetero atoms such as sulfur, nitrogen, oxygen, phosphorus and the like. Further, they can contain one or more substituents such as thiol, hydroxy, nitro, amino, nitrile, amide, ester and halogen groups and others. Such organic radicals may contain aryl groups, such as aralkyl and alkaryl groups. The preferred organic radicals are free of olefinic or alkynyl unsaturation and generally have up to about 20, preferably up to about 10 carbon atoms. Particularly preferred amides are urea, thiourea, formamide, biuret, triuret, thioformamide, ethyl formamide, methyl formamide, and combinations of these.

The chalcogens are elements of Periodic Group VI-B and include oxygen, sulfur, selenium, tellurium, and polonium. Oxygen and sulfur are presently preferred due to low cost, availability, low toxicity and chemical activity, with oxygen the most preferred.

The combination of agents can be used for immediate and long-term, pre- and postemergent control of essentially any form of vegetation. The combination of agents of the present invention is particularly useful as a defoliating agent. It may be used, for example, in tree nurseries, fruit and vegetable cultivations, legumes, grapevines, roses, and in particular, cotton. The plants or plant parts to be harvested are thereby made both more accessible in an advantageous manner and also are accelerated considerably in their ripening. In certain cases and under proper environmental conditions, plants thus treated in time will reform sound, normal foliage.

The combination of agents of the present invention is particularly suited for defoliating cotton plants, making it possible to an extent not previously obtained to use picking machines for the harvest. It is a particular advantage of the present invention that other defoliating agents are not required. The claimed combination both defoliates the cotton plant and substantially inhibits regrowth of new leaves for a substantial period of time. This latter aspect is particularly important where the cotton cannot be harvested within a short time of treatment.

The combination of the present invention also may be used advantageously for the control of vegetation. The efficacy for growth control depends, among other things, on the amount of the combination applied per acre, the treatment time, and the type of plant to which it is applied. The inhibiting effects may occur in a manner which produces, for example, total inhibition of development (destruction) of a waste blend floral including shrubbery. The combination of agents of the invention also can be used wherever it is desired not to fully destroy a floral at once, but to maintain it in a vegetative low growth stage.

Illustrative of vegetation that can be controlled by these methods, with or without the use of surfactants are: black mustard (*brassica nigra*), curly dock (*rumex crispus*), common groundsel (*senecio vulgaris*), pineapple weed (*matricaria matricarioides*), swamp smartweed (kelp) (*polygonum coccineum*), prickly lettus (*lactuca scariola*), lance-leaved groundcherry (*physalis lanceifolia*), annual sowthistle (*sonchus oleraceus*), london rocket (*sisymbrium irio*), common fiddleneck (*amsinckia intermedia*), hairy nightshade (*solanum sarrachoides*), shepherd's purse (*capsella bursa-pastoris*), sunflower (*helianthus annus*), common knotweed (*polygonum aviculare*), green amaranth (*amaranthus hybridus*), mare's tail (*conyza canadensis*), henbit (*lamium amplexicaule*), cocklebur (*xanthium strumarium*), cheeseweed (*malva parviflora*), lambsquarters (*chenopodium album*), puncture vine (*tribulus terrestris*), common purslane (*portulaca oleracea*), prostrate spurge (*euphorbia supina*), telegraph plant (*heterotheca grandiflora*), carpetweed (*mollugo verticillata*), yellow starthistle (*centaurea solstitialis*), milk thistle (*silybum marianum*), mayweed (*anthemis cotula*), burning nettle (*urtica urens*), fathen (*atriplex patula*), chickweed (*stellaria media*), scarlet pimpernel (*anagallis arvensis*) redroot pigweed (*amaranthus retroflexus*), minnerslettuce (*montia perfoliata*), turkey mullein (*eremocarpus setigerus*), nettleleaf goosefoot (*chenopodium murale*), prostrate pigweed (*amaranthus blitoides*), silverleaf nightshade (*solanum elaeagnifolium*), hoary cress (*cardaria draba*), largeseed dodder (*cuscuta indecora*), California burclover (*medicago polymorpha*), horse purslane (*trianthema portulacastrum*), field bindweed (*Iconvolvulus arvensis*), Russian knapweed (*centaurea repens*), flax-leaved fleabane (*conyza bonariensis*), wild radish (*raphanus sativus*), tumble pigweed (*amaranthus albus*), stephanomeria (*stephanomeria exigua*), wild turnip (*brassica campestris*), buffalo goard (*cucurbita foetidissima*), common mullein (*verbascum thapsus*), dandelion (*taraxacum officinale*), Spanish thistle (*xanthium spinosum*), chicory (*cichorium intybus*), sweet anise (*foeniculum vulgare*), annual yellow sweetclover (*melilotus indica*), poison hemlock (*conium maculatum*), broadleaf filaree (*erodium botrys*), whitestem filaree (*erodium moschatum*), redstem filaree (*erodium cicutarium*), ivyleaf morning-glory (*ipomea hederacea*), shortpod mustard (*brassica geniculata*), buckhorn plantain (*plantago lacenolata*), sticky chickweed (*cerastium viscosum*), himalaya blackberry (*rubus procerus*), purslane speedwell (*veronica peregrina*), Mexican tea (*chenopodium ambrosioides*), Spanish clover (*lotus purshianus*), Australian brassbuttons (*cotula australis*), goldenrod (*solidago californica*), citron (*citrullus lanatus*), hedge mustard (*sisymbrium orientale*), black nightshade (*solanum nodiflorum*), Chinese thornapple (*datura ferox*), bristly ox tongue (*picris echioides*), bull thistle (*cirsium vulgare*), spiny sowthistle (*sonchus asper*), Tasmanian goosefoot (*chenopodium pumilio*), goosefoot (*chenopodium botrys*), wright groundcherry (*physalis acutifolia*), tomatillo groundcherry (*physalis philadelphica*), pretty spurge (*euphorbia peplus*), bitter apple (*cucumis myriocarpus*), indian tobacco (*nicotiana bigelovii*), common morning-glory (*ipomoea purpurea*), waterplantain (*alisma triviale*), smartweed (*polygonum lapathifolium*), mature sowthistle (*sonchus asper*), yellow nutsedge (*cyperus esculentus*), purple nutsedge (*cyperus rotundus*), lupine (*lupinus formosus*), and grasses of the family Gramineae such as annual rye grass, blue grass, water grass, barnyard grass, bermuda grass, fescue, mat grass, Johnson grass, and the like.

The amide-sulfuric acid adduct can be produced by the reaction of the amide with sulfuric acid by the methods described in U.S. Pat. No. 4,445,925, the disclosure of which is incorporated in its entirety by reference.

While the combination of the present invention can be used alone, it generally is applied to plants in conjunction with other substances, such as a carrier vehicle, wetting agents, emulsifiers, solvents and the like. Suitable carrier vehicles include water, aliphatic or aromatic hydrocarbons, such as benzene, toluene, xylene, cyclohexonone, isophorone, and mineral oil or vegetable fractions. The particularly preferred carrier vehicle is water, based on its availability and cost. Alternatively, of course, a solid carrier vehicle could be utilized. Examples of solid carrier vehicles are minerals, such as siliceous clay, silica gel, talc, kaolin, limestone, and plant products, such as flours.

Typical surface active substances, which may be utilized included calcium-lignin sulfonate, polyoxyethyleneoctylphenol ether and naphthalene-sulfonic acids and their salts, phenosulfonic acids and their salts, formaldehyde condensates, fatty alcohol sulfates, and substituted benzenesulfonic acids and their salts.

The proportions of the active agents in the composition of the present invention may vary within wide limits. For example, the composition may contain from about 10 to 80 weight percent of the active agents, and about 20 to 90 weight percent of a solid or liquid carrier vehicle, and optionally up to 20 weight percent of a surface-active substance.

The ratio of adduct to abscission agent also may vary widely. The abscission agents, for use in the present invention, are typically in the form of a wetable powder comprising a certain weight percent of the abcission agent. whereas the adduct is generally sold in a carrier liquid comprising a specified weight percent of the adduct. The ratios are expressed in terms of a weight of adduct to weight of abscission agent. Broadly, the ratio of adduct to abscission agent is in the range of from about 2:1 to as high as about 400:1. More typically, the ratio will be within the range of from about 6:1 to 200:1, with a preferred range being from about 12:1 to 100:1 (pounds per pound based on the active ingredient, i.e., lb. of adduct per lb. of abscission agent exclusive of any inert carrier).

The combination of the present invention has been found to be highly effective for defoliation of plants, such as cotton, when the ratio of the adduct to abscission agent is selected such that, when applied, the amount of adduct applied per acre is within the range of from about 0.6 to 26 pounds, preferably from 1.3 to 10 pounds, and more preferably within the range of from about 0.2 to 5 pounds per acre, and the amount of abscission agent applied per acre is within the range of about 0.01 to 0.3, preferably from 0.05 to 0.2 pounds per acre, and more preferably about 0.075 to 0.15 pounds per acre.

To facilitate a uniform distribution of the composition of the invention on plants to be treated, it generally is applied in a carrier vehicle. As hereinbefore mentioned, water is the preferred carrier vehicle. When the composition is sprayed from the ground, typically, it is diluted with water to provide a spray volume of from 1 to 200, and more typically 10 to 50 gallons per acre. In the case of aerial spraying, a more concentrated solution is used and is applied at the rate of from about 2 to 8, and more generally 3 to 5 gallons per acre.

The following example and test data therein are for illustrative purposes only and should not be construed as limiting the scope of the invention.

EXAMPLE

To demonstrate the efficacy of the present invention, a series of field tests was performed. The abscission agent utilized was thidiazuron, sold commercially in the form of a wettable powder and containing approximately 50 weight percent of the active ingredient. It is sold for use as a cotton defoliant and registered for such purpose with the Environmental Protection Agency. The adduct used is a commercially available monocarbamide dihydrogen sulfate (MCDS) herbicide registered with the Environmental Protection Agency for use on a variety of plants. It is sold in a liquid form and comprises about 82 weight percent (10.4 pounds per gallon) of the active ingredient. Each was applied alone and in various combinations to cotton plants. The plants were approximately 30 inches tall having approximately 60 percent open boil. In each instance, the agents were dilute with water to provide a spray volume of approximately 25 gallons per treated acre. Visual ratings of the percent defoliation obtained were made seven days after treatment (DAT). The results are set forth in Table 1.

TABLE 1

| No. | Treatment | Rep | 7 DAT % Defol. |
|---|---|---|---|
| 1 | MCDS (2 gal.) | 1 | 25 |
| | | 2 | 20 |
| | | 3 | 20 |
| | | Avg. | 22 |
| 2 | MCDS (3 gal.) | 1 | 35 |
| | | 2 | 30 |
| | | 3 | 25 |
| | | Avg. | 30 |
| 3 | MCDS (5 gal.) | 1 | 35 |
| | | 2 | 25 |
| | | 3 | 30 |
| | | Avg. | 30 |
| 4 | MCDS (10 gal.) | 1 | 65 |
| | | 2 | 50 |
| | | 3 | 40 |
| | | Avg. | 52 |
| 5 | Thidiazuron (0.1 lb.) | 1 | 40 |
| | | 2 | 35 |
| | | 3 | 35 |
| | | Avg. | 37 |
| 6 | Thidiazuron (0.2 lb.) | 1 | 50 |
| | | 2 | 40 |
| | | 3 | 50 |
| | | Avg. | 47 |
| 7 | MCDS & Thidiazuron (1 gal. + 0.1 lb.) | 1 | 90 |
| | | 2 | 98 |
| | | 3 | 95 |
| | | Avg. | 94 |
| 8 | MCDS & Thidiazuron (1 gal. + 0.2 lb.) | 1 | 95 |
| | | 2 | 90 |
| | | 3 | 98 |
| | | Avg. | 94 |
| 9 | MCDS & Thidiazuron (2 gal. + 0.1 lb.) | 1 | 95 |
| | | 2 | 95 |
| | | 3 | 98 |
| | | Avg. | 96 |
| 10 | MCDS & Thidiazuron (2 gal. + 0.2 lb.) | 1 | 98 |
| | | 2 | 95 |
| | | 3 | 95 |
| | | Avg. | 96 |
| 11 | MCDS & Thidiazuron (3 gal. + 0.1 lb.) | 1 | 98 |
| | | 2 | 95 |
| | | 3 | 95 |
| | | Avg. | 96 |
| 12 | MCDS & Thidiazuron (3 gal. + 0.2 lb.) | 1 | 95 |
| | | 2 | 98 |
| | | 3 | 90 |
| | | Avg. | 94 |

For purposes of cotton defoliation, any percent defoliation of less than 90 percent generally is deemed unacceptable by the growers. From Table 1, it is seen that monocarbamide dihydrogen sulfate (MCDS), even when applied in amounts as high as 10 gallons per acre, does not produce satisfactory defoliation. In a similar manner, thidiazuron when applied in amounts of from 0.1 to 0.2 pounds per acre provide inadequate defoliation. However, in all instances, the combination of monocarbamide dihydrogen sulfate (MCDS) and thidiazuron resulted in excess of 90 percent defoliation. The foregoing table clearly demonstrates the synergistic effect of the claimed combination.

In addition, it should be noted that the rate at which the commercial formulation of monocarbamide dihydrogen sulfate normally is applied is from a minimum of 5 up to as high as 20 gallons per acre. In a similar manner, the normal or recommended application rate for commercial formulations of thidiazuron is from about 0.2 of a pound up to about 0.4 pound per acre for defoliation. As shown in Table I, the application of 0.10 pound of thidiazuron produced only 37 percent defoliation (treatment No. 5). One gallon of monocarbamide dihydrogen sulfate would hardly produce any visible results on cotton. Indeed, as shown by treatment No. 1, 2 gallons per acre results in only 22 percent defoliation. Nonetheless, as shown by treatment No. 7, 1 gallon of monocarbamide dihydrogen sulfate and 0.10 pound of thidiazuron produced substantially in excess of 90 percent defoliation.

A second field test was conducted to verify the results obtained above. The same agents were utilized and diluted to provide the same 25 gallon per acre application rate. The results of this second field test are set forth in Table II. From that Table it is seen, again, that the claimed combination exhibits a synergistic effect and provides in excess of about 90 percent defoliation.

TABLE II

| | | | % Defoliation | | |
|---|---|---|---|---|---|
| No. | Treatment | Rep | 6 DAT | 10 DAT | 14 DAT |
| 1 | Thidiazuron (0.10 lb.) | 1 | 20 | 50 | 60 |
| | | 2 | 25 | 40 | 60 |
| | | 3 | 20 | 40 | 60 |
| | | Avg. | 22 | 43 | 60 |
| 2 | Thidiazuron (0.20 lb.) | 1 | 35 | 70 | 85 |
| | | 2 | 30 | 75 | 90 |
| | | 3 | 35 | 70 | 85 |
| | | Avg. | 33 | 72 | 87 |
| 3 | MCDS + Thidiazuron (2 qt. + 0.1 lb.) | 1 | 90 | 95 | 98 |
| | | 2 | 80 | 80 | 95 |
| | | 3 | 95 | 95 | 90 |
| | | Avg. | 88 | 90 | 94 |
| 4 | MCDS + Thidiazuron (4 qt + 0.1 lb.) | 1 | 90 | 98 | 98 |
| | | 2 | 98 | 98 | 98 |
| | | 3 | 95 | 98 | 98 |
| | | Avg. | 94 | 98 | 98 |
| 5 | MCDS + Thidiazuron (8 qt. + 0.1 lb.) | 1 | 90 | 95 | 98 |
| | | 2 | 90 | 90 | 95 |
| | | 3 | 95 | 95 | 98 |
| | | Avg. | 92 | 93 | 97 |

A third field test was conducted to determine the effect of varying the ratio of adduct to abscission agent. The adduct and abscission agent utilized wee the same as in the previous test. In each instance, they were further diluted with water to provide an application rate of 25 gallons per acre. The cotton treated was immature and actively growing which is more difficult to defoliate and inhibit regrowth. Leaf counts were taken three and seven days after treatment (DAT). Application No. 16 was a material currently considered by the growers as a standard against which other formulations are judged. It comprised a mixture of 20 oz. tribufos (an organo phosphate defoliant) and a small amount of thidiazuron (0.063 pounds active ingredient) per acre. The organo phosphate is the principal defoliant, and the thidiazuron is used to inhibit regrowth of leaves. While the organo phosphates are effective defoliants, they have an unpleasant odor and have been subject to some environmental concern. Thus, a replacement for the organo phosphates is desirable.

The results of the test set forth in Tables III and IV clearly demonstrate the efficacy of the present invention over a wide range of ratios. More particularly, from those tables, it is seen that the claimed combination is as effective or more effective in defoliating cotton plants than the standard material used in application No. 16. Specifically, the average number of leaves remaining on the plants is approximately equal to or less than the average number of leaves on plants treated with the "standard" (No. 16) defoliant.

TABLE III

| No. | Rate/Acre[1] Commercial Formulation | | | 3 DAT Leaves/Plant[2] | | | | |
|---|---|---|---|---|---|---|---|---|
| | MCDS | Thidiazu | Ratio | I | II | III | IV | Avg |
| 1 | 8 oz | 0.050 lb. | 2.6:1 | 4.6 | 4.4 | 4.8 | 5.2 | 4.75 |
| 2 | 16 | 0.10 | | 4.0 | 3.0 | 4.4 | 3.6 | 3.75 |
| 3 | 32 | 0.20 | | 2.6 | 4.0 | 4.2 | 4.4 | 3.80 |
| 4 | 16 | 0.05 | 26:1 | 3.8 | 4.8 | 3.4 | 3.0 | 3.75 |
| 5 | 32 | 0.10 | | 2.6 | 2.2 | 2.8 | 3.2 | 2.70 |
| 6 | 64 | 0.20 | | 3.6 | 3.0 | 2.0 | 2.0 | 2.65 |
| 7 | 24 | 0.05 | 39:1 | 3.0 | 3.0 | 3.6 | 2.8 | 3.10 |
| 8 | 48 | 0.10 | | 2.4 | 2.8 | 2.2 | 3.2 | 2.65 |
| 9 | 96 | 0.20 | | 3.0 | 3.0 | 3.0 | 1.8 | 2.70 |
| 10 | 32 | 0.050 | 52:1 | 4.2 | 3.0 | 3.6 | 2.4 | 3.30 |
| 11 | 64 | 0.10 | | 2.4 | 2.4 | 2.6 | 2.4 | 2.45 |
| 12 | 128 | 0.20 | | 3.2 | 2.2 | 3.0 | 2.4 | 2.70 |
| 13 | 0 | 0.050 | n/a | 7.2 | 8.2 | 6.4 | 6.8 | 7.15 |
| 14 | 0 | 0.10 | | 5.8 | 3.4 | 4.4 | 3.8 | 4.35 |
| 15 | 0 | 0.20 | | 3.4 | 4.0 | 4.4 | 4.6 | 4.10 |
| 16 | STD 20 oz. | 0.063 | n/a | 4.4 | 4.4 | 4.6 | 5.2 | 4.65 |

[1]Ratio of lbs MCDS:lb of thidiazuron. The commercial MCDS formulations comprise = 81.6 wt. percent active ingredient MCDS (10.4 lb./gal) and the thidiazuron formulations comprise 50 wt. percent thidiazuron.
[2]The average was computed from a total of 20 observations (4 replicates × 5 observations each). Observations consisted of randomly selecting five plants from the middle two rows of each plot and counting the remaining primary leaves (axillary branches and leaves were NOT counted).

TABLE IV

| No. | Rate/Acre[3] Commercial Formulation | | | 7 DAT Leaves/Plant[2] | | | | |
|---|---|---|---|---|---|---|---|---|
| | MCDS | Thidiazu | Ratio | I | II | III | IV | Avg |
| 1 | 8 oz | 0.050 lb. | 2.6:1 | 4.5 | 3.3 | 3.7 | 3.5 | 3.75 |
| 2 | 16 | 0.10 | | 2.3 | 2.7 | 2.7 | 1.7 | 2.35 |
| 3 | 32 | 0.20 | | 1.8 | 1.7 | 1.0 | 2.7 | 1.80 |
| 4 | 16 | 0.05 | 26:1 | 2.5 | 3.2 | 2.0 | 2.5 | 2.55 |
| 5 | 32 | 0.10 | | 0.3 | 1.3 | 0.7 | 0.7 | 0.75 |
| 6 | 64 | 0.20 | | 2.0 | 2.0 | 0.5 | 0.8 | 1.33 |
| 7 | 24 | 0.050 | 39:1 | 2.2 | 2.7 | 2.0 | 1.2 | 2.03 |
| 8 | 48 | 0.10 | | 0.7 | 0.5 | 0.2 | 0.5 | 0.48 |
| 9 | 96 | 0.20 | | 1.5 | 1.3 | 1.7 | 1.7 | 1.55 |
| 10 | 32 | 0.050 | 52:1 | 2.7 | 3.0 | 1.0 | 3.0 | 2.43 |
| 11 | 64 | 0.10 | | 0.5 | 1.2 | 0.3 | 0.3 | 0.58 |
| 12 | 128 | 0.20 | | 1.8 | 1.7 | 1.8 | 2.3 | 1.90 |
| 13 | 0 | 0.050 | n/a | 5.0 | 6.5 | 5.0 | 4.5 | 5.25 |
| 14 | 0 | 0.10 | | 3.7 | 2.7 | 3.7 | 3.0 | 3.28 |
| 15 | 0 | 0.20 | | 2.5 | 3.0 | 3.0 | 2.5 | 2.75 |
| 16 | STD | 0.063 | n/a | 3.5 | 3.0 | 3.5 | 4.0 | 3.50 |

[1]Ratio of lbs MCDS:lb of thidiazuron. The commercial MCDS formulations comprise = 81.6 wt. percent active ingredient MCDS (10.4 lb./gal) and the thidiazuron formulations comprise 50 wt. percent thidiazuron.
[2]The average was computed from a total of 20 observations (4 replicates × 5 observations each). Observations consisted of randomly selecting five plants from the middle two rows of each plot and counting the remaining primary leaves (axillary branches and leaves were NOT counted).

While particular embodiments of this invention have been described, it will be understood that the invention is not limited thereto. Many modifications can be made. For example, while the invention has been described with respect to the two particularly preferred compounds, and their use on cotton, it will be readily apparent to those skilled in the art that other combinations within the scope of the invention can be utilized on cotton and on other plants as well. The application rates per acre and ratios have been expressed in pounds of active ingredients of the preferred compounds for the reader's convenience in practicing the invention. When compounds having substantially different molecular weights (MCDS=158 and thidiazuron=220), the application rates and weight ratios are readily adjusted to reflect the differences in molecular weight. It is intended that such modifications as will fall within the spirit and scope of the appended claims are included.

What is claimed is:

1. A composition for controlling vegetation comprising thidiazuron and monocarbide dihydrogen sulfate, wherein the ratio of monocarbamide dihydrogen sulfate to thidiazuron in the composition is about 2 pounds of monocarbamide dihydrogen sulfate per pound of thidiazuron to about 400 pounds of monocarbamide dihydrogen sulfate per pound of thidiazuron.

2. The composition of claim 1 wherein the ratio of monocarbamide dihydrogen sulfate to thidiazuron in the composition is about 6 pounds of monocarbamide dihydrogen sulfate per pound of thidiazuron to about 200 pounds of monocarbamide dihydrogen sulfate per pound of thidiazuron.

3. The composition of claim 2 further comprising about 20 to 90 weight percent of a carrier vehicle.

4. The composition of claim 3 wherein the carrier vehicle is water.

5. The composition of claim 1 wherein the ratio of monocarbamide dihydrogen sulfate to thidiazuron in the composition is about 12 pounds of monocarbamide dihydrogen sulfate per pound of thidiazuron to about 100 pounds of monocarbamide dihydrogen sulfate per pound of thidiazuron.

6. A mixture of thidiazuron, monocarbamide dihydrogen sulfate and water, wherein the ratio of monocarbamide dihydrogen sulfate to thidiazuron in the mixture is about 2 pounds of monocarbamide dihydrogen sulfate per pound of thidiazuron to about 400 pounds of monocarbamide dihydrogen sulfate per pound of thidiazuron.

7. A method for controlling vegetation comprising the step of applying to the vegetation an effective amount of a composition formed by mixing thidiazuron and monocarbamide dihydrogen sulfate, wherein the amount of monocarbamide dihydrogen sulfate applied per acre is about 0.2 to 26 pounds and the amount of thidiazuron applied per acre is about 0.01 to about 0.3 pounds.

8. The method of claim 7 wherein the amount of monocarbamide dihydrogen sulfate applied per acre is about 0.6 to 10 pounds.

9. The method of claim 7 wherein the amount of monocarbamide dihydrogen sulfate applied per acre is about 1.3 to 5 pounds.

10. The method of claim 7 wherein the amount of thidiazuron applied per acre is about 0.05 to about 0.2 pounds.

11. The method of claim 7 wherein the amount of thidiazuron applied per acre is about 0.075 to about 0.15 pounds.

12. The method of claim 7 wherein the amount of monocarbamide dihydrogen sulfate applied per acre is about 0.6 to 10 pounds and the amount of thidiazuron applied per acre is about 0.05 to about 0.2 pounds.

13. The method of claim 7 wherein the amount of monocarbamide dihydrogen sulfate applied per acre is about 1.3 to 5 pounds and the amount of thidiazuron applied per acre is about 0.075 to about 0.15 pounds.

14. The method of claim 7 wherein the vegetation is cotton.

15. The method of claim 7 wherein the composition is applied at spray volume of 1 to 200 gallons per acre.

16. The method of claim 7 wherein the composition is applied at spray volume of about 2 to 50 gallons per acre.

17. A method for controlling vegetation comprising the step of applying to the vegetation an effective amount of a composition formed by mixing thidiazuron and monocarbamide dihydrogen sulfate, wherein the ratio of monocarbamide dihydrogen sulfate to thidiazuron in the composition is about 2 pounds of monocarbamide dihydrogen sulfate per pound of thidiazuron to about 400 pounds of monocarbamide dihydrogen sulfate per pound of thidiazuron.

18. The method of claim 17 wherein the ratio of monocarbamide dihydrogen sulfate to thidiazuron in the composition is about 6 pounds of monocarbamide dihydrogen sulfate per pound of thidiazuron to about 200 pounds of monocarbamide dihydrogen sulfate per pound of thidiazuron.

19. The method of claim 17 wherein the ratio of monocarbamide dihydrogen sulfate to thidiazuron in the composition is about 12 pounds of monocarbamide dihydrogen sulfate per pound of thidiazuron to about 100 pounds of monocarbamide dihydrogen sulfate per pound of thidiazuron.

20. The method of claim 17 wherein the amount of monocarbamide dihydrogen sulfate applied per acre is about 0.2 to 26 pounds.

21. The method of claim 17 wherein the amount of monocarbamide dihydrogen sulfate applied per acre is about 0.6 to 10 pounds.

22. The method of claim 17 wherein the amount of monocarbamide dihydrogen sulfate applied per acre is about 1.3 to 5 pounds.

23. The method of claim 17 wherein the amount of thidiazuron applied per acre is about 0.05 to about 0.2 pounds.

24. The method of claim 17 wherein the amount of thidiazuron applied per acre is about 0.01 to about 0.3 pounds.

25. The method of claim 17 wherein the amount of thidiazuron applied per acre is about 0.075 to about 0.15 pounds.

26. The method of claim 17 wherein the amount of monocarbamide dihydrogen sulfate applied per acre is about 0.6 to 10 pounds and the amount of thidiazuron applied per acre is about 0.05 to about 0.2 pounds.

27. The method of claim 17 wherein the amount of monocarbamide dihydrogen sulfate applied per acre is about 1.3 to 5 pounds and the amount of thidiazuron applied per acre is about 0.075 to about 0.15 pounds.

28. The method of claim 17 wherein the vegetation is cotton.

29. The method of claim 17 wherein the composition is applied at spray volume of 1 to 200 gallons per acre.

30. The method of claim 17 wherein the composition is applied at spray volume of about 2 to 50 gallons per acre.

* * * * *

UNITED STATES PATENT AND TRADEMARK OFFICE
CERTIFICATE OF CORRECTION

PATENT NO. : 5,238,905

DATED : August 24, 1993

INVENTOR(S) : Mark L. Atwater

It is certified that error appears in the above-identified patent and that said Letters Patent is hereby corrected as shown below:

Claim 1, column 10, line 11, replace "monocarbide" with -- monocarbamide --.

Signed and Sealed this

Twelfth Day of April, 1994

Attest:

BRUCE LEHMAN

Attesting Officer   Commissioner of Patents and Trademarks